US010878938B2

(12) United States Patent
Kural

(10) Patent No.: US 10,878,938 B2
(45) Date of Patent: Dec. 29, 2020

(54) SYSTEMS AND METHODS FOR ANALYZING SEQUENCE DATA

(71) Applicant: Seven Bridges Genomics Inc., Charlestown, MA (US)

(72) Inventor: Deniz Kural, Somerville, MA (US)

(73) Assignee: Seven Bridges Genomics Inc., Charlestown, MA (US)

( * ) Notice: Subject to any disclaimer, the term of this patent is extended or adjusted under 35 U.S.C. 154(b) by 467 days.

(21) Appl. No.: 15/809,153

(22) Filed: Nov. 10, 2017

(65) Prior Publication Data
US 2018/0232483 A1 Aug. 16, 2018

Related U.S. Application Data

(63) Continuation of application No. 14/177,958, filed on Feb. 11, 2014, now Pat. No. 9,817,944.

(51) Int. Cl.
G16B 30/00 (2019.01)
G16B 45/00 (2019.01)
C12Q 1/6869 (2018.01)
C12Q 1/6883 (2018.01)

(52) U.S. Cl.
CPC ............ G16B 30/00 (2019.02); C12Q 1/6869 (2013.01); C12Q 1/6883 (2013.01); G16B 45/00 (2019.02); C12Q 2521/301 (2013.01)

(58) Field of Classification Search
CPC ...... G16B 30/00; G16B 45/00; C12Q 1/6869; C12Q 1/6883
USPC .......................................................... 702/19
See application file for complete search history.

(56) References Cited

U.S. PATENT DOCUMENTS

| 5,511,158 | A | 4/1996 | Sims |
| 5,701,256 | A | 12/1997 | Marr et al. |
| 6,054,278 | A | 4/2000 | Dodge et al. |
| 6,223,128 | B1 | 4/2001 | Allex et al. |
| 7,577,554 | B2 | 8/2009 | Lystad et al. |
| 7,580,918 | B2 | 8/2009 | Chang et al. |
| 7,809,509 | B2 | 10/2010 | Milosavljevic |
| 7,885,840 | B2 | 2/2011 | Sadiq et al. |
| 7,917,302 | B2 | 3/2011 | Rognes |
| 8,209,130 | B1 | 6/2012 | Kennedy et al. |
| 8,340,914 | B2 | 12/2012 | Gatewood et al. |
| 8,370,079 | B2 | 2/2013 | Sorenson et al. |
| 8,639,847 | B2 | 1/2014 | Blaszczak et al. |
| 9,063,914 | B2 | 6/2015 | Kural et al. |
| 9,092,402 | B2 | 7/2015 | Kural et al. |
| 9,116,866 | B2 | 8/2015 | Kural |
| 9,390,226 | B2 | 7/2016 | Kural |
| 9,817,944 | B2 | 11/2017 | Kural |
| 2004/0023209 | A1 | 2/2004 | Jonasson |
| 2005/0089906 | A1 | 4/2005 | Furuta et al. |
| 2006/0292611 | A1 | 12/2006 | Berka et al. |
| 2007/0166707 | A1 | 7/2007 | Schadt et al. |
| 2008/0077607 | A1 | 3/2008 | Gatawood et al. |
| 2008/0294403 | A1 | 11/2008 | Zhu et al. |
| 2009/0119313 | A1 | 5/2009 | Pearce |
| 2009/0164135 | A1 | 6/2009 | Brodzik et al. |
| 2009/0300781 | A1 | 12/2009 | Bancroft et al. |
| 2010/0041048 | A1 | 2/2010 | Diehl et al. |
| 2010/0169026 | A1 | 7/2010 | Sorenson et al. |
| 2011/0004413 | A1 | 1/2011 | Carnevali et al. |
| 2011/0096193 | A1 | 4/2011 | Egawa |
| 2011/0098193 | A1 | 4/2011 | Kingsmore et al. |
| 2012/0041727 | A1 | 2/2012 | Mishra et al. |
| 2012/0045771 | A1 | 2/2012 | Beier et al. |
| 2012/0239706 | A1 | 9/2012 | Steinfadt |
| 2012/0330566 | A1 | 12/2012 | Chaisson |
| 2013/0059738 | A1 | 3/2013 | Leamon et al. |
| 2013/0059740 | A1 | 3/2013 | Drmanac et al. |
| 2013/0073214 | A1 | 3/2013 | Hyland et al. |
| 2013/0124100 | A1 | 5/2013 | Drmanac et al. |
| 2013/0289099 | A1 | 10/2013 | Goff et al. |
| 2013/0311106 | A1 | 11/2013 | White et al. |
| 2014/0025312 | A1 | 1/2014 | Chin et al. |
| 2014/0051588 | A9 | 2/2014 | Drmanac et al. |
| 2014/0066317 | A1 | 3/2014 | Talasaz |
| 2014/0136120 | A1 | 5/2014 | Colwell et al. |
| 2014/0200147 | A1 | 7/2014 | Bartha et al. |
| 2014/0278590 | A1 | 9/2014 | Abbassi et al. |
| 2014/0280360 | A1 | 9/2014 | Webber et al. |
| 2014/0323320 | A1 | 10/2014 | Jia et al. |
| 2015/0056613 | A1 | 2/2015 | Kural |
| 2015/0057946 | A1 | 2/2015 | Kural |
| 2015/0094212 | A1 | 4/2015 | Gottimukkaia et al. |
| 2015/0110754 | A1 | 4/2015 | Bai et al. |
| 2015/0112602 | A1 | 4/2015 | Kural et al. |
| 2015/0112658 | A1 | 4/2015 | Kural et al. |

(Continued)

FOREIGN PATENT DOCUMENTS

WO 2012096579 A3 7/2012
WO 2012098515 A1 7/2012
(Continued)

OTHER PUBLICATIONS

Agarwal, 2013, SINNET: Social Interaction Network Extractor from Text, Proc IJCNLP 33-36.
(Continued)

Primary Examiner — Jerry Lin
(74) Attorney, Agent, or Firm — Wolf, Greenfield & Sacks, P.C.

(57) ABSTRACT

The invention provides methods for comparing one set of genetic sequences to another without discarding any information within either set. A set of genetic sequences is represented using a directed acyclic graph (DAG) avoiding any unwarranted reduction to a linear data structure. The invention provides a way to align one sequence DAG to another to produce an alignment that can itself be stored as a DAG. DAG-to-DAG alignment is a natural choice wherever a set of genomic information consisting of more than one string needs to be compared to any non-linear reference. For example, a subpopulation DAG could be compared to a population DAG in order to compare the genetic features of that subpopulation to those of the population.

20 Claims, 10 Drawing Sheets

Specification includes a Sequence Listing.

(56) References Cited

U.S. PATENT DOCUMENTS

| | | |
|---|---|---|
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0227685 A1 | 8/2015 | Kural |
| 2015/0293994 A1 | 10/2015 | Kelly |
| 2015/0302145 A1 | 10/2015 | Kural et al. |
| 2015/0310167 A1 | 10/2015 | Kural et al. |
| 2015/0344970 A1 | 12/2015 | Vogelstein et al. |
| 2015/0347678 A1 | 12/2015 | Kural |
| 2015/0356147 A1 | 12/2015 | Mishra et al. |
| 2016/0259880 A1 | 9/2016 | Semenyuk |
| 2016/0306921 A1 | 10/2016 | Kural |
| 2016/0364523 A1 | 12/2016 | Locke et al. |
| 2017/0058320 A1 | 3/2017 | Locke et al. |
| 2017/0058341 A1 | 3/2017 | Locke et al. |
| 2017/0058365 A1 | 3/2017 | Locke et al. |
| 2017/0198351 A1 | 7/2017 | Lee et al. |
| 2017/0199959 A1 | 7/2017 | Locke |
| 2017/0199960 A1 | 7/2017 | Ghose et al. |
| 2017/0242958 A1 | 8/2017 | Brown |

FOREIGN PATENT DOCUMENTS

| | | |
|---|---|---|
| WO | 2012142531 A2 | 10/2012 |
| WO | 2015027050 A1 | 2/2015 |
| WO | 20/5058095 A1 | 4/2015 |
| WO | 2015048753 A1 | 4/2015 |
| WO | 2015058093 A1 | 4/2015 |
| WO | 2015058097 A1 | 4/2015 |
| WO | 2015058120 A1 | 4/2015 |
| WO | 2015061099 A1 | 4/2015 |
| WO | 2015061103 A1 | 4/2015 |
| WO | 2015105963 A1 | 7/2015 |
| WO | 2015123269 A1 | 8/2015 |
| WO | 2016141294 A1 | 9/2016 |
| WO | 2016201215 A1 | 12/2016 |
| WO | 2017120128 A1 | 7/2017 |
| WO | 2017123864 A1 | 7/2017 |
| WO | 2017147124 A1 | 8/2017 |

OTHER PUBLICATIONS

Aguiar, 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13): i352-i360.
Airoldi, 2008, Mixed membership stochastic blockmodels, JMLR 9:1981-2014.
Albers, 2011, Dindel: Accurate indel calls from short-read data, Genome Research 21:961-973.
Alioto et al., A comprehensive assessment of somatic mutation detection in cancer using whole-genome sequencing, Nature Communications, Dec. 9, 2015.
Altera, 2007, Implementation of the Smith-Waterman algorithm on reconfigurable supercomputing platform, White Paper ver 1.0 (18 pages).
Altschul, 1986, Optimal Sequence Alignment Using Affine Gap Costs, Bull Math Biol 48(5/6):603-616.
Bansal, 2008, An MCMC algorithm for haplotype assembly from whole-genome sequence data, Genome Res 18:1336-1346.
Bao, 2013, BRANCH: boosting RNA-Seq assemblies with partial or related genomic sequences, Bioinformatics 29 (10):1250-1259.
Barbieri, 2013, Exome sequencing identifies recurrent SPOP, FOXA1 and MED12 mutations in prostate cancer, Nature Genetics 44:6 685-689.
Beerenwinkel, 2007, Conjunctive Bayesian Networks, Bernoulli 13(4), 893-909.
Berlin, 2014, Assembling large genomes with single-molecule sequencing and locality sensitive hashing, bioRxiv preprint (35 pages); retrieved from the internet on Jan. 29, 2015, at.

Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.
Browning et al, Haplotype phasing: existing methods and new developments, 2011, vol. 12, Nature Reviews Genetics.
Caboche et al, Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pp. iii31-iii38, vol. 21, Oxford University Press.
Chang, 2005, The application of alternative splicing graphs in quantitative analysis of alternative splicing form from EST database, Int J Comp Appl Tech 22(1):14.
Chin, 2013, Nonhybrid finished microbial genome assemblies from long-read SMRT sequencing data, Nat Meth 10 (6):563-569.
Chuang, 2001, Gene recognition based on DAG shortest paths, Bioinformatics 17(Suppl. 1):s56-s64.
Compeau, 2011, How to apply de Bruijn graphs to genome assembly, Nat Biotech 29(11):987-991.
Craig, 1990, Ordering of cosmid clones covering the Herpes simplex virus type 1 (HSV-I) genome: a test case for fingerprinting by hybridisation, Nucleic Acids Research 18:9 pp. 2653-2660.
Denoeud, 2004, Identification of polymorphic tandem repeats by direct comparison of genome sequence from different bacterial strains: a web-based resource, BMC Bioinformatics 5:4 pp. 1-12.
DePristo, 2011, A framework for variation discovery and genotyping using next-generation DNA sequencing data, Nat Gen 43:491-496.
Duan et al., Optimizing de novo common wheat transcriptome assembly using short-read RNA-Seq data. (2012) pp. 1-12, vol. 13, BMC Genomics.
Dudley, 2009, A quick guide for developing effective bioinformatics programming skits, PLoS Cornput Biol 5(12): e1000589.
Durbin, 2014, Efficient haplotype matching and storage using the positional Burrows-Wheeler transform (PBWT), Bioinformatics 30(9):1266-1272.
Endelman, 2011, New algorithm improves fine structure of the barley consensus SNP map, BMC Genomics 12(1):407 (and whole document).
Exam Report issued in EP14803268.3.
Examination Report issued in SG 11201601124Y.
Extended European Search Report issued in EP 14837955.5.
Extended European Search Report issued in EP 14847490.1.
Extended European Search Report issued in EP 14854801.9.
Farrar, 2007, Striped Smith-Waterman speeds database searches six times over other SIMD implementations, Bioinformatics 23(2):156-161.
Fitch, 1970, Distinguishing homologous from analogous proteins, Systematic Zoology 19:99-113.
Flicek, 2009, Sense from sequence reads: methods for alignment and assembly, Nat Meth Supp; 6(11s):s6-s12.
Garber, 2011, Computational methods for transcriptome annotation and quantification using RNA-Seq, Nat Meth 8 (6):469-477.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp. 531-537.
Gotoh, 1982, An improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29 (7):644-654.
Grasso, 2004, Combining partial order alignment and progressive multiple sequence alignment increases alignment speed and scalability to very large alignment problems, Bioinformatics 20(10):1546-1556.

(56) References Cited

OTHER PUBLICATIONS

Guttman, 2010, Ab initio reconstruction of cell type-specific transcriptomes in mouse reveals the conserved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, Nih-PA Author Manuscript.
Haas, 2004, DAGchainer: a tool for mining segmental genome duplications and synteny, Bioinformatics 20 (18):3643-3646.
Harrow, 2012, GENCODE: The reference human aenome annotation for The ENCODE Project, Genome Res 22:1760-1774.
He, 2010, Optimal algorithms for haplotype assembly from whole-genome sequence data, Bioinformatics 26:i183-i190.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Homer, 2010, Improved variant discovery through local re-alignment of short-read next generation sequencing data using SRMA, Genome Biol 11(10):R99.
Horspool, 1980, Practical Fast Searching in Strings, Software—Practice & Experience 10:501-506.
Huang, Chapter 3: Bio-Sequence Comparison and Alignment, ser. Curr Top Comp Mol Biol. Cambridge, Mass.: The MIT Press, 2002.
Hutchinson, 2014, Allele-specific methylation occurs at genetic variants associated with complex diseases, PLoS One 9(6):e98464.
International Search Report and Written Opinion dated Aug. 31, 2017, for International Application No. PCT/US2017/018830 with International Filing Date Feb. 22, 2017, (11 pages).
International Search Report and Written Opinion dated Mar. 31, 2015 for International Application No. PCT/US2015/010604 filed Jan. 8, 2015 (13 pages).
International Search Report and Written Opinion dated Apr. 19, 2017 for International Patent Application No. PCT/US2017/012015, (14 Pages).
International Search Report and Written Opinion dated Feb. 17, 2015, for International Patent Application No. PCT/US2014/061156, filed Oct. 17, 2014 (19 pages).
International Search Report and Written Opinion dated Jan. 10, 2017, for International Patent Application No. PCT/US16/57324 with International Filing Date Oct. 17, 2016, (7 pages).
International Search Report and Written Opinion dated Mar. 19, 2015, for International Patent Application No. PCT/US2014/061162 with International Filing Date Oct. 17, 2014, (12 pages).
International Search Report and Written Opinion dated May 11, 2015, for International Patent Application No. PCT/US2015/015375 with International Filing Date Feb. 11, 2015, (12 pages).
International Search Report and Written Opinion dated May 5, 2016, for International Patent Application No. PCT/US2016/020899, wiht International Filing Date Mar. 4, 2016, (12 pages).
International Search Report and Written Opinion dated Apr. 7, 2017, for International Patent Application No. PCT/US17/13329, filed Jan. 13, 2017, (9 pages).
International Search Report and Written Opinion dated Dec. 11, 2014, for International Patent Application No. PCT/US14/52065, filed Aug. 21, 2014, (18 pages).
International Search Report and Written Opinion dated Dec. 30, 2014, for International Patent Application No. PCT/US14/58328, filed Sep. 30, 2014, (22 pages).
International Search Report and Written Opinion dated Feb. 4, 2015, for International Patent Application No. PCT/US2014/061198, filed Oct. 17, 2014, (8 pages).
International Search Report and Written Opinion dated Feb. 10, 2015, for International Patent Application No. PCT/US2014/060690, filed Oct. 15, 2014, (11 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
International Search Report and Written Opinion dated Sep. 2, 2016, for International Patent Application No. PCT/US16/57324 with International Filing Date May 19, 2016, (14 pages).
International Search Report and Written Opinion dated Sep. 7, 2016, for International Patent Application No. PCT/US16/57324 with International Filing Date Jun. 10, 2016, (8 pages).
Kano, 2010, Text mining meets workflow: linking U-Compare with Taverna, Bioinformatics 26(19):2486-7.
Kehr, 2014, Genome alignment with graph data structures: a comparison, BMC Bioinformatics 15:99.
Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Koolen, 2008, Clinical and Molecular Delineation of the 17q21.31 Microdeletion Syndrome, J Med Gen 45(11):710-720.
Kumar, 2010, Comparing de novo assemblers for 454 transcriptome data, BMC Genomics 11:571.
Kurtz, 2004, Versatile and open software for comparing large genomes, Genome Biol 5:R12.
Lam, 2008, Compressed indexing and local alignment of DNA, Bioinformatics 24(6):791-97.
Langmead, 2009, Ultrafast and memory-efficient alignment of short DNA sequences to the human genome; Genome Biol 10:R25.
Larkin, 2007, Clustal W and Clustal X version 2.0, Bioinformatics 23(21):2947-2948.
Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, Accurate read mapping using a graph-based human pan-genome, ASHG 2014 Abstracts.
LeGault, 2010, Learning Probalistic Splice Graphs from RNA-Seq data, pages.cs.wisc.edu/~legauit/cs760_writeup.pdf; retrieved from the Internet on Apr. 6, 2014.
LeGault, 2013, Inference of alternative splicing from RNA-Seq data with probabilistic splice graphs, Bioinformatics 29 (18):2300-2310.
Leipzig, 2004, The alternative splicing gallery (ASG): Bridging the gap between genome and transcriptome, Nuc Acids Res 23(13):3977-3983.
Li, 2009, Fast and accurate short read alignment with Burrows-Wheeler Transform. Bioinformatics 25:1754-60.
Li, 2010, A survey of sequence alignment algorithms for next-generation sequencing, Briefings in Bionformatics 11 (5):473-483.
Lipman, 1985, Rapid and sensitive protein similarity searches, Science 227(4693):1435-41.
Lucking, 2011, PICS-Ord: unlimited coding of ambiguous regions by pairwise identity and cost scores ordination, BMC Bioinf 12:10.
Lupski, 2005, Genomic disorders: Molecular mechanisms for rearrangements and conveyed phenotypes, PLoS Genetics 1(6):e49.
Ma, 2010, Multiple genome alignment based on longest path in directed acyclic graphs, Int J Bioinformatics 6(4):366-683.

(56) References Cited

OTHER PUBLICATIONS

Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived from the Internet on Jun. 3, 2016, at.
Marth et al., 1999—A general approach to single-nucleotide polymorphism discovery, pp. 452-456, vol. 23, Nature Genetics.
Mazrouee, 2014, FastHap: fast and accurate single individual haplotype reconstructions using fuzzy conflict graphs, Bioinformatics 30:i371-i378.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Mount, 2001, Multiple Sequence Alignment, Bioinformatics, 2001, Cold Spring Harbor Laboratory Press, Cold Spring Harbor, New York, pp. 139-204.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.
Nagarajan, 2013, Sequence assembly demystified, Nat Rev 14:157-167.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Newman, 2013, Community detection and graph portioning, Europhys Lett 103(2):28003, arXiv:1305.4974v1.
Newman, 2014, An ultrasensitive method for quantitating circulating tumor DNA with broad patient coverage, Nature Medicine 20:5 1-11.
Olsson, 2015, Serial monitoring of circulating tumor DNA in patients with primary breast cancer for detection of occult metastatic disease. EMBO Molecular Medicine 7:8 1034-1047.
Oshlack, 2010, From RNA-seq reads to differential expression results. Genome Bio 11:220.
Parks, 2015, Detecting non-allelic homologous recombination from high-throughput sequencing data, Genome Biol 16:17.
Peixoto, 2014, Efficient Monte Carlo and greedy heuristic for the inference of stochastic block models; Phys. Rev. E 89, 012804.
Pop et al., 2004, Comparative genome assembly, Briefings in Bioinformatics vol. 5, pp. 237-248.
Pruesse, 2012, SINA: Accurate high-throughput multiple sequence alignment of ribosomal RNA genes, Bioinformatics 28:14 1823-1829.
Rajaram, 2013, Pearl millet [*Pennisetum glaucum* (L.) R. Br.] consensus linkage map constructed using four RIL mapping populations and newly developed EST-SSRs, BMC Genomics 14(1):159.
Raphael, 2004, A novel method for multiple alignment of sequences with repeated and shuffled elements, Genome Res 14:2336-2346.
Robertson, 2010, De novo assembly and analysis of RNA-seg data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with intersequence SIMD parallelisation, Bioinformatics 12:221.
Ronquist, 2012, MrBayes 3.2: efficient Bayesian phylogenetic inference and model choice across a large model space, Syst Biol 61(3):539-42.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central)Bioinformatics 9(318).
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions; Disc Appl Mat 127:95-117.
Shao, 2006; Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 2012, Multiple insert size paired-end sequencing for deconvolution of complex transcriptions, RNA Bio 9(5) 596-609.
Sosa, 2012, Next-Generation Sequencing of Human Mitochondrial Reference Genomes Uncovers High Heteroplasmy Frequency, PLoS One 8(10):e1002737.
Sturgeon, RCDA: a highly sensitive and specific alternatively spliced transcript assembly tool featuring upstream consecutive exon structures, Genomics, Dec. 2012, 100(6): 357-362.
Subramanian, 2008, DIALIGN-TX: greedy and progessive approaches for segment-based multiple sequence alignment, Alg Mol Biol 3(1):1-11.
Sudmant, 2015, An integrated map of structural variation in 2,504 human genomes, Nature 526:75-81.
Sun, 2006, Pairwise Comparison Between Genomic Sequences and Optical maps, dissertation. New York University (131 pages); retreived from the Internet on Jun. 3, 2016, at.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tarhio, 1993, Approximate Boyer-Moore String Matching, SIAM J Comput 22(2):243-260.
Thomas, 2014, Community-wide effort aims to better represent variation in human reference genome, Genome Web (11 pages).
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Wang, 2009, RNA-Seq: a revolutionary tool for transcriptomics, Nat Rev Genet 10(1):57-63.
Written Opinion issued in SG 11201601124Y.
Written Opinion issued in SG 11201602903X.
Written Opinion issued in SG 11201603039P.
Written Opinion issued in SG 11201603044S.
Written Opinion issued in SG 11201605506Q.
Wu, 2010, Fast and SNP-tolerant detection of complex variants and splicing in short reads, Bioinformatics, 26 (7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.

(56) References Cited

OTHER PUBLICATIONS

Yanovsky, 2008, Read mapping algorithms for single molecule sequencing data, Proc 8th Int Workshop Alg Bioinformatics 5251:38-49.

Yu, 2010, The construction of a tetraploid cotton genome wide comprehensive reference map, Genomics 95:230-240.

Zeng, 2013, PyroHMMvar: a sensitive and accurate method to call short indels and SNPs for Ion Torrent and 454 data, Bioinformatics 29:22 2859-2868.

Zhang et al., Construction of a high-density genetic map for sesame based on large scale marker development by specific length amplified fragment (SLAF) sequencing. (2013) pp. 1-12, vol. 13, BMC Plant Biology.

TTGGATATGGG (SEQ ID NO: 1)
TTGGATCGAATTATGGG (SEQ ID NO: 2)

FIG. 2

GATTACACATGATTACATGACTGACCATTCCAT (SEQ ID NO: 3)
GAGTACAGATTACATGACTGACGGAGCATTACATCT (SEQ ID NO: 4)

GATTACACATGATTACATGACTGACCATTCCAT (SEQ ID NO: 3)
GAGTACA---GATTACATGACTGACGGAGCATTACATCT (SEQ ID NO: 4)

GATTACACATGATTACATGACTGACCATTCCAT (SEQ ID NO: 3)
GAGTACA---GATTACATGACTGACGGAGCATTACATCT (SEQ ID NO: 4)

GATTACACATGATTACATGACTGAC----CATTCCAT (SEQ ID NO: 3)
GAGTACA---GATTACATGACTGACGGAGCATTACATCT (SEQ ID NO: 4)

GATTACACATGATTACATGACTGAC----CATTCCAT (SEQ ID NO: 3)
GAGTACA---GATTACATGACTGACGGAGCATTACATCT (SEQ ID NO: 4)

SEQUENCE LISTING

```
<160> NUMBER OF SEQ ID NOS: 4

<210> SEQ ID NO 1
<211> LENGTH: 11
<212> TYPE: DNA
<213> ORGANISM: Homo sapiens

<400> SEQUENCE: 1
ttggatatgg g                                                         11

<210> SEQ ID NO 2
<211> LENGTH: 17
<212> TYPE: DNA
<213> ORGANISM: Homo sapiens

<400> SEQUENCE: 2
ttggatcgaa ttatggg                                                   17

<210> SEQ ID NO 3
<211> LENGTH: 33
<212> TYPE: DNA
<213> ORGANISM: Homo sapiens

<400> SEQUENCE: 3
gattacacat gattacatga ctgaccattc cat                                 33

<210> SEQ ID NO 4
<211> LENGTH: 36
<212> TYPE: DNA
<213> ORGANISM: Homo sapiens
```

```
<400> SEQUENCE: 4
gagtacagat tacatgactg acggagcatt acatct                                                    36
```

SYSTEMS AND METHODS FOR ANALYZING SEQUENCE DATA

CROSS-REFERENCE TO RELATED APPLICATION

This application is a continuation of U.S. patent application Ser. No. 14/177,958, filed on Feb. 11, 2014 (now U.S. Pat. No. 9,817,944), the contents of which are hereby incorporated by reference in its entirety.

SEQUENCE LISTING

This application contains a sequence listing which has been submitted in ASCII format via EFS-Web and is hereby incorporated by reference in its entirety. The ASCII-formatted sequence listing, created on Apr. 30, 2018, is named SBG-004-01US-Sequences ST25, and is 880 bytes in size.

FIELD OF THE INVENTION

The invention relates to analysis of genetic and genomic sequences.

BACKGROUND

Much information about a person's health is encoded in their DNA. Next-generation sequencing (NGS) technologies rapidly translate that information from its natural, biological format into files of sequence data that can be examined for disease-associated mutations and other features. However, as DNA sequencing technologies become faster, cheaper, and more accurate, the results produced by those sequencing technologies can become difficult to analyze.

It is now often the case that a researcher or medical professional will have to make sense of raw sequence data that is more complex than the linear sequence of "a gene" or even "a genome". Most genomic sequencing produces millions of reads that must be assembled together in order to make sense of the data. Due to heterozygosity, somatic mutations, repeated genetic elements, structural variants, sequencing errors, or other factors, sequence reads can be assembled in many ways, some of which have little, or even misleading, informatics content.

Moreover, genomic sequencing is often more complex than simply sequencing an individual's genome. For example, researchers will study whole populations of related subjects, or will need to compare those results from one study with those results from another. Unfortunately, comparing one set of results with another often requires data-limiting simplifications. For example, reads are often assembled and then reduced to a consensus sequence for comparison to a reference, thus potentially ignoring sources of heterogeneity within those reads.

Some attempts have been made to represent genetic information using a data structure known as a directed acyclic graph (DAG). However, while a DAG can potentially represent known instances of heterogeneity, simply having a DAG does not address the problem of what to do with numerous complex sets of sequence data.

SUMMARY

The invention provides methods for comparing one set of genetic sequences to another without discarding any information within either set or otherwise sacrificing the breadth of information within either set of sequences for the sake of making the comparison. The invention includes methods of aligning two or more DAGs in order to produce an aligned DAG. The aligned DAG is simply the aligned combination of two or more DAGs and is similar to any of the original DAGs except that the input to the aligned DAG is always two or more DAGs as opposed to linear sequence. The aligned DAG can further be aligned to other DAGs or other aligned DAGs as described below.

Methods of the invention are useful to obtain a best-scoring DAG alignment based on weighted scores for matches, mis-matches, and gaps and can find the best scoring alignment even where each of the input sequence data sets to be aligned is structured to represent numerous different nucleotides or sequences at numerous different locations along a genome, that is, where each input sequence set is a structured as a non-linear representation of a plurality of aligned sequences such as a genomic sequence DAG.

Methods of the invention are useful to store sets of genetic sequences as a sequence DAG. A sequence DAG may be used to represent any multi-plex set of related nucleic acid or protein sequences such as, for example, a multiple sequence alignment of related genes, an assembly of NGS reads, or two or more reference genomes. Furthermore, methods of the invention may be used to align one sequence DAG to another, wherein the resulting alignment can be represented as a sequence DAG that can potentially represent a full multiple sequence alignment among all of the individual sequences that contributed to one of the paths through one of the initial sequence DAGs.

DAG-to-DAG alignment is a natural choice for many urgent applications. It is appropriate wherever a set of genomic information consisting of more than one string needs to be compared to any non-linear reference. For example, a subpopulation DAG could be compared to a population DAG in order to compare the genetic features of that subpopulation to those of the population. Similarly, a cancer DAG could be compared to a species, population, subpopulation, or familial DAG. In view of the fact that the progression of cancer may be viewed as rapid, numerous mutations in the genome, a DAG representing certain types of cancers may give a better understanding not only of the cause of cancer but of the cancer itself.

In certain aspects, the invention provides a method for genomic analysis. The method includes representing a plurality of nucleic acids as a reference directed acyclic graph (DAG), wherein a DAG comprises nodes, each node comprising a string of one or more nucleotides, and edges defining connections among the nodes, and further wherein one or more of the nodes each represent more than one of the plurality of nucleic acids. The method further includes obtaining a second DAG representing a second plurality of nucleic acids and finding an optimally-scoring alignment between the second DAG and the reference DAG. The second DAG can be obtained from any suitable source such as, for example, sequence reads from a sample from a subject. The reference DAG may represent a plurality of alleles associated with a disease.

Preferably the steps are performed using a computer system comprising a processor coupled to a non-transitory memory having the reference DAG stored therein and further wherein the optimally-scoring alignment is stored as a final DAG in the non-transitory memory. A DAG may be stored as a computer file in which each node comprises a character string and a label and each edge comprises a pair of labels.

Finding the best-scoring alignments between a reference DAG and a second DAG may be done by initializing a matrix or matrices with the nucleotides of the first DAG on one side or and those of the second DAG on the other side. As the figures indicate, representing this two-dimensionally can be difficult, because each DAG is itself more than one-dimensional and those DAGs do not map easily onto linear sides of matrices. However, the equations described herein describe straightforward recursive relationships between the matrix elements. The matrix cell with the highest value is identified after that recursive process is complete, and a path through the matrix is identified ending at that cell (e.g., using Smith-Waterman-type "backtracking" techniques). This path indicates the optimally-scoring or best-scoring alignment between the second DAG and the reference DAG.

In some embodiments, at least one path through the reference DAG represents a sequence of a human chromosome. At least one path through the second DAG may represent an alternative sequence of the human chromosome. Homozygous loci in the sample may be represented using a single node in the second DAG and heterozygous loci in the sample are represented using different nodes in the second DAG. In certain embodiments, the second DAG represents a transcriptome from an organism and the reference DAG represents one or more genomes from organisms of a same species as the organism. In some embodiments, the reference DAG comprises a plurality of binary alignment map (BAM) entries that have been mapped to a first genomic reference and the second DAG comprises a second plurality of BAM entries that have been mapped to a second genomic reference.

Aspects of the invention provide a method of identifying chromosomal structural variants. The method includes obtaining a plurality of paired-end reads from a nucleic acid sample, each comprising an upstream pair member and a downstream pair member and characterized by an insert length approximating a number of nucleotides spanning a distance from an upstream end of the upstream pair member to a downstream end of the downstream pair member. The upstream pair member of each of the plurality of paired-end reads is mapped to a reference. A subset of the plurality of paired-end reads for which the upstream pair members map to the reference within a pre-defined cluster is found. For the subset of the plurality of paired-end reads, the downstream pair members are assembled into a DAG that represents one or more chromosomal structural variants within the sample.

In other aspects, the invention provides a method of identifying haplotypes. The method includes obtaining a plurality of sequence reads from a number k of diploid genomes, assembling the reads into a DAG representing optimally-scoring alignments among the sequence reads, and determining support for each of a plurality of paths through the DAG according to a number of reads consistent with a location in that path that is consistent with fewer reads than any other location in that path. A number of the paths meeting some pre-determined support criteria are identified as describing relevant haplotypes. In some embodiments, the pre-determined support criteria includes identifying a number n of paths for which the support meets a constraint and identifying the min(n, k) best-supported of the paths as the relevant haplotypes.

BRIEF DESCRIPTION OF THE DRAWINGS

FIG. 2 shows the actual matrices that correspond to the comparison.

DETAILED DESCRIPTION

Figure 1:
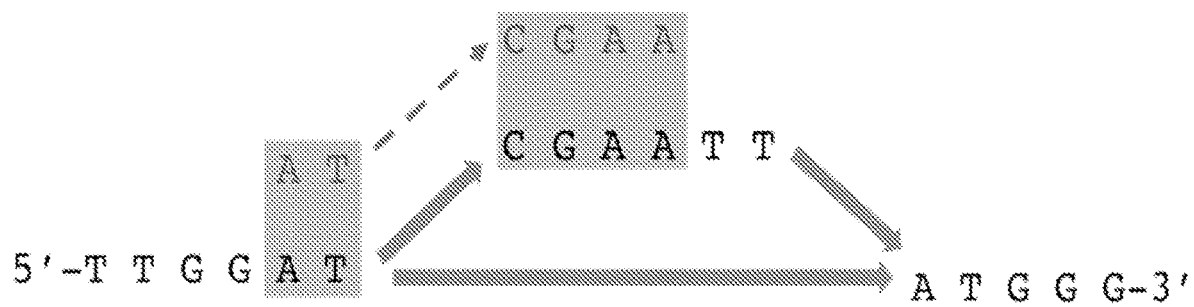
FIG. 1 represents a read being compared to a DAG.

Embodiments of the invention provide for the alignment of one sequence DAG to another sequence DAG. A DAG is a mathematical data structure that may be represented as a graph, but that is not necessarily ever instantiated as a visible graph. A DAG is a data structure that has nodes connected by directed edges, wherein no single path through the DAG traverses the same node more than once and thus does not include any cycles. "DAG" can refer to a graph, the underlying data structure, or both, and as used herein, "sequence DAG" refers to a DAG representing biological sequences. A sequence DAG may be a record stored in a non-transitory, computer-readable medium that includes nodes connected by edges, in which each node includes a string of one or more nucleotide characters with a 5'-3' directionality and each edge extends from a 3' end of the character string of one node to a 5' end of a string of another node. At least one node will be a source in that it has no edges connected to the 5' end of its character string. At least one node will be a sink in that it has no edges connected to the 3' end of its character string. What characters are permitted may depend on the embodiment or implementation, and in some embodiments, the permitted characters include the IUPAC nucleotide codes (either A, T, C, and G, with or without U or N, or the complete set of IUPAC ambiguity codes).

1. Alignments

The invention provides methods for aligning one or more sequence DAGs to one another. Alignment generally involves placing one sequence along another sequence, gaps may be introduced along each sequence, scoring how well the two sequences match, and preferably repeating for various position along one or more of the sequences. The best-scoring match is deemed to be the alignment and represents an inference about the historical relationship between the sequences. Some analysis projects may seek an optimal scoring alignment that is not also a highest scoring alignment, and methods of the invention may be used to find the optimally scoring alignment. For example, where gene duplication has created copies of a gene that descend side by side during the history of an organism, (e.g., alpha and beta hemoglobin) the genes may be called paralogous genes. Fitch, 1970, Distinguishing homologous from analogous proteins, Systematic Zoology 19:99-113. A researcher studying two paralogous genes in an organism's genome may obtain sequence reads from one of those genes. The researcher may wish to compare a sequence read DAG from the one gene to a genomic DAG that represents a plurality of known genomes for that organism. In some instances, the read DAG may have a higher-scoring alignment to the second, paralogous gene (e.g., due to mutations in the researcher's sample) than to the one gene. In that sense, the researcher has a priori information that the alignment of the read DAG to the one gene in the genomic DAG is the optimal alignment, even though it is not the highest-scoring or best-scoring alignment. Methods of the invention may be used to find that optimal alignment by excluding the other alignment results from consideration. Thus the invention provides methods that may be used to find an alignment between two or more sequence DAG. In some embodiments, the resulting aligned DAG will represent an optimal alignment. That optimal alignment may be a best-scoring DAG matrix alignment produced by a combination of the two sequence-DAGs. The best-scoring DAG alignment may be determined by the mathematical construct as described herein, representing the optimal path through a matrix of similarity scores.

In a pairwise alignment, a base in one sequence alongside a non-matching base in another indicates that a substitution mutation has occurred at that point. Similarly, where one sequence includes a gap alongside a base in the other sequence, an insertion or deletion mutation (an "indel") may be inferred to have occurred.

In some embodiments, scoring an alignment of a pair of nucleic acid sequences involves setting values for the probabilities of substitutions and indels. When individual bases are aligned, a match or mismatch contributes to the alignment score by a score or a penalty, which could be, for example, a match score of 1 for a match and a mismatch penalty of −0.33 for a mismatch. An indel deducts from an alignment score by a gap penalty, which could be, for example, −1. Scores and penalties can be based on empirical knowledge or a priori assumptions about how sequences evolve. Their values affects the resulting alignment. Particularly, the relationships among score and penalty values influence whether substitutions or indels will be favored in the resulting alignment. Additional helpful discussion may be found in Rodelsperger, 2008, Syntenator: Multiple gene order alignments with a gene-specific scoring function, Alg Mol Biol 3:14; Yanovsky, et al., 2008, Read mapping algorithms for single molecule sequencing data, Procs of the 8th Int Workshop on Algorithms in Bioinformatics 5251: 38-49; Hein, 1989, A new method that simultaneously aligns and reconstructs ancestral sequences for any number of homologous sequences, when phylogeny is given, Mol Biol Evol 6(6):649-668; Schwikowski & Vingron, 2002, Weighted sequence graphs: boosting iterated dynamic programming using locally suboptimal solutions, Disc Appl Mat 127:95-117, the contents of each of which are incorporated by reference.

Stated formally, a pairwise alignment represents an inferred relationship between two sequences, x and y. For example, in some embodiments, a pairwise alignment A of sequences x and y maps x and y respectively to another two strings x' and y' that may contain spaces such that: (i)|x'|=|y'|; (ii) removing spaces from x' and y' should get back x and y, respectively; and (iii) for any i, x'[i] and y'[i] cannot be both spaces.

A gap is a maximal substring of contiguous spaces in either x' or y'. Pairwise alignment A can include the following three kinds of regions: (i) matched pair (e.g., x'[i]=y'[i]; (ii) mismatched pair, (e.g., x'[i]≠y'[i] and both are not spaces); or (iii) gap (e.g., either x'[i..j] or y'[i..j] is a gap). In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

In some embodiments, any pair has a score a defined by a 4×4 matrix B of scores/penalties. For example, B[i,i]=1 and 0<B(i,j)i< >j<1 is one possible scoring system. For instance, where a transition is thought to be more biologically probable than a transversion, matrix B could include B[C,T]=0.7 and B[A,T]=0.3, or any other set of values desired or determined by methods known in the art.

Alignment according to some embodiments of the invention generally involves—for sequence Q (query) having m characters and a reference genome T (target) of n characters—finding and evaluating possible local alignments between Q and T. For any 1≤i≤n and 1≤j≤m, the largest possible alignment score of T[h..i] and Q[k..j], where h≤i and k≤j, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol, 48(3):443-453, 1970) and Smith-Waterman (J Mol Biol, 147(1):195-197, 1981; Adv. in Math. 20(3), 367-387, 1976). A further improvement to Smith-Waterman by Gotoh (J Mol Biol, 162(3), 705-708, 1982) reduces the calculation time from O(m2n) to O(mn) where m and n are the sequence sizes being compared and is more amendable to parallel processing. In the field of bioinformatics, it is Gotoh's modified algorithm that is often referred to as the Smith-Waterman algorithm.

Smith-Waterman-type algorithms align linear sequences by rewarding overlap between bases in the sequences, and penalizing gaps between the sequences. Smith-Waterman also differs from Needleman-Wunsch, in that Smith-Waterman does not require the shorter sequence to span the string of letters describing the longer sequence. That is, Smith-Waterman does not assume that one sequence is a read of the entirety of the other sequence. Furthermore, because Smith-Waterman is not obligated to find an alignment that stretches across the entire length of the strings, a local alignment can begin and end anywhere within the two sequences. Smith-Waterman algorithms, and implementations thereof, are described in more detail in U.S. Pat. No. 5,701,256 and U.S. Pub. 2009/0119313, both herein incorporated by reference in their entirety.

Smith-Waterman type algorithms may be used to perform a pairwise alignment of two sequences a and b of length n and m by first calculating values for entries h[i,j] in an n×m matrix H of similarity (or distance) scores and then finding a trace through that matrix according to the steps described below. First, the matrix is initialized by assigning h[i,0]=h[0,j]=0, for 0≤i≤n and 0≤j≤m. Note that i and j are indices of a and b so that a[i] is the ith nucleotide in a.

Then, for each remaining entry h[i,j], the neighbors to the left, above, and to the above-left of that entry are evaluated to find the highest scoring one of those entries. In a two dimensional matrix (e.g., during pairwise alignment), those three cells to the left, above, and diagonally to the left and above h[i,j] would be h[i−1,j], h[i,j−1], and h[i−1,j−1].

An association is recorded between that entry h[i,j] and the highest valued of h[i−1,j], h[i,j−1], and h[i−1,j−1]. A value is calculated for h[i,j] based on the value of that associated entry. The association can be thought of as a pointer from entry h[i,j] to its highest-valued neighbor, and this pointer will be "looked at" later, when it used to find a trace through the matrix. The value assigned to h[i,j] is:

$$\max\{h[i-1,j-1]+s(a[i],b[j]),h[i-1,j]-W,h[i,j-1]-W,0\} \quad (1)$$

In the equations above, s(a[i],b[j]) represents either a match bonus (when a[i]=b[j]) or a mismatch penalty (when a[i]≠b[j]), and W represents a penalty for gap in either a or b. Gap penalty W may preferably include an opening component and an extension component, discussed later.

Once values have been assigned for every entry h[i,j] in H, a trace is found through the matrix by the following steps. First, the highest-valued entry h[i,j] is identified. Then—remembering that each entry is associated with one upstream neighbor—entries in H are traced sequentially from the highest-valued entry following the associations, or "pointers", until a zero entry is reached. The resulting trace will originate at the highest-valued entry and extend "back" (i.e., towards h[0,0]) to its terminus at the first zero entry encountered by following the pointers. That trace (sometimes called a traceback in the literature) indicates the optimally-scoring alignment between the sequences a and b. That is, the optimally-scoring alignment can be read by writing out the indices of each entry in the trace in their order within the trace and supplying a "–" character where the trace extends off-diagonal, and then using the indices as indices of a and b to retrieve the corresponding nucleotide characters from a and b. Thus if a trace extends through h[3,3], h[4,4], h[4,5], h[4,6], h[5,7], the paired indices will be:

3 4 - - 5
3 4 5 6 7

Smith-Waterman type alignment may be employed using dynamic programming. This dynamic programming technique employs tables or matrices to preserve match scores and avoid re-computation for successive cells.

To formalize the foregoing description for programming, and to give an example set of values for the bonuses and penalties, the following steps are given. Note that in the above, a single gap penalty was used. In the below, separate insertion and deletion penalties are tracked. Either approach may be used and one of skill in the art may choose one over the other for extrinsic reasons such as a priori knowledge of likelihoods of certain sequence evolution events.

Each element of a string is indexed with respect to a letter of the sequence, that is, if S is the string ATCGAA, S[1]=A. For a matrix B, entries B[j,k] are given in equation (2) below:

$$B[j,k]=\max(p[j,k],i[j,k],d[j,k],0) \text{ (for } 0<j\le m, 0\le k\le n) \quad (2)$$

The arguments of the maximum function, B[j,k], are outlined in equations (3)-(5) below, wherein MISMATCH_PENALTY, MATCH_BONUS, INSERTION_PENALTY, DELETION_PENALTY, and OPENING_PENALTY are all constants, and all negative except for MATCH_BONUS. The match argument, p[j,k], is given by equation (3), below:

$$p[j,k]=\max(p[j-1,k-1],i[j-1,k-1],d[j-1,k-1])+\text{MISMATCH\_PENALTY, if } S[j]\neq A[k]=\max(p[j-1,k-1],i[j-1,k-1],d[j-1,k-1])+\text{MATCH\_BONUS, if } S[j]=A[k] \quad (3)$$

the insertion argument i[j,k], is given by equation (4), below:

$$i[j,k]=\max(p[j-1,k]+\text{OPENING\_PENALTY},i[j-1,k],d[j-1,k]+\text{OPENING\_PENALTY})+\text{INSERTION\_PENALTY} \quad (4)$$

and the deletion argument d[j,k], is given by equation (5), below:

$$d[j,k]=\max(p[j,k-1]+\text{OPENING\_PENALTY},i[j,k-1]+\text{OPENING\_PENALTY},d[j,k-1])+\text{DELETION\_PENALTY} \quad (5)$$

For all three arguments, the [0,0] element is set to zero to assure that the backtrack goes to completion, i.e., p[0,0]=i[0,0]=d[0,0]=0.

The scoring parameters may be adjusted according to the project. One example of the scoring parameter settings (Huang, Chapter 3: Bio-Sequence Comparison and Alignment, ser. Curr Top Comp Mol Biol. Cambridge, Mass.: The MIT Press, 2002) for nucleic acids would be:
MATCH_BONUS: 10
MISMATCH_PEN: −20
INSERTION_PEN: −40
OPENING_PEN: −10
DELETION_PEN: −5

The relationship between the gap penalties (INSERTION_PENALTY, OPENING_PENALTY) above help limit the number of gap openings, i.e., favor grouping gaps together, by setting the gap insertion penalty higher than the gap opening cost. Of course, alternative relationships between MISMATCH_PENALTY, MATCH_BONUS, INSERTION_PENALTY, OPENING_PENALTY and DELETION_PENALTY are possible.

2. Sequence DAG Alignments

The foregoing describes a formalism of a Smith-Waterman type alignment that is conducive to implementation by dynamic programming. One benefit of the invention includes the insight that the alignment algorithm, thus formalized, may be extended to a non-linear sequence structure such as a sequence DAG. Such an extended implementation may be referred to as a multi-dimensional Smith-Waterman type alignment. Such multi-dimensional algorithms of the invention provide for a "look-back" through a multi-dimensional space that includes multiple pathways and multiple nodes. The multi-dimensional algorithm identifies the maximum score at each position on the DAG (e.g., the reference sequence construct). In fact, by looking "backwards" at the preceding positions, it is possible to identify the optimum alignment across a plurality of possible paths.

A sequence DAG may be stored as a list of nodes and edges. One way to do this is to create a text file that includes all nodes, with an ID assigned to each node, and all edges, each with the node ID of starting and ending node. Thus, for example, were a DAG to be created for two sentences, "See Jane run," and "Run, Jane run,", a case-insensitive text file could be created. Any suitable format could be used. For example, the text file could include comma-separated values. Naming this DAG "Jane" for future reference, in this format, the DAG "Jane" may read as follows: 1 see, 2 run, 3 jane, 4 run, 1-3, 2-3, 3-4. One of skill in the art will appreciate that this structure is easily applicable to the sequences represented in FIGS. 1 and 7, for example, and the accompanying discussion below.

In certain embodiments, a DAG is stored as a table representing a matrix (or an array of arrays or similar variable structure representing a matrix) in which the (i,j) entry in the matrix denotes whether node i and node j are connected. For the DAG to be acyclic simply requires that all non-zero entries be above the diagonal (assuming indices are correctly ordered). In a binary case, a O entry represents that no edge is exists from node i to node j, and a 1 entry represents an edge from i to j. One of skill in the art will appreciate that a matrix structure allows values other than O to 1 to be associated with an edge. For example, any entry may be a numerical value indicating a weight, or a number of times used, reflecting some natural quality of observed data in the world. A matrix can be written to a text file as a table or a linear series of rows (e.g., row 1 first, followed by a separator, etc.), thus providing a simple serialization structure.

One useful way to serialize a matrix DAG would be to use comma-separated values for the entries, after defining the nodes. Using this format, the DAG "Jane" would include the same node definitions as for above, followed by matrix entries. This format could read as:

1 see, 2 run, 3 jane, 4 run
,,1, \,, 1, \,,, 1\,,, where zero (0) entries are simply omitted and '\' is a newline character.

Embodiments of the invention include storing a sequence DAG in a language built with syntax for graphs. For example, The DOT Language provided with the graph visualization software package known as Graphviz provides a data structure that can be used to store a DAG with auxiliary information and that can be converted into graphic file formats using a number of tools available from the Graphviz web site. Graphviz is open source graph visualization software. Graph visualization is a way of representing structural information as diagrams of abstract graphs and networks. It has important applications in networking, bioinformatics, software engineering, database and web design, machine learning, and in visual interfaces for other technical domains. The Graphviz programs take descriptions of graphs in a simple text language, and make diagrams in useful formats, such as images and SVG for web pages; PDF or Postscript for inclusion in other documents; or display in an interactive graph browser.

In an intermediate extension of Smith-Waterman type alignments, a sequence string is aligned to a sequence DAG, and a discussion of this will aid in understanding and implementing a full DAG-to-DAG alignment.

For aligning a string to a DAG, let S be the string being aligned, and let D be the directed acyclic graph to which S is being aligned. The elements of the string, S, are bracketed with indices beginning at 1. Thus, if S is the string ATCGAA, S[1]=A, S[4]=G, etc.

In certain embodiments, for the DAG, each letter of the sequence of a node will be represented as a separate element, d. A predecessor of d is defined as:

(i) If d is not the first letter of the sequence of its node, the letter preceding d in its node is its (only) predecessor;

(ii) If d is the first letter of the sequence of its node, the last letter of the sequence of any node (e.g., all residues upstream in the 16S rRNA gene) that is a parent of d's node is a predecessor of d.

The set of all predecessors is, in turn, represented as P[d].

In order to find the "best" alignment, the algorithm seeks the value of M[j,d], the score of the optimal alignment of the first j elements of S with the portion of the DAG preceding (and including) d. This step is similar to finding $H_{i,j}$ in equation 1 above. Specifically, determining M[j,d] involves finding the maximum of a, i, e, and 0, as defined below:

$$M[j,d]=\max\{a,i,e,0\}$$

where $$e=\max\{M[j,p^*]+\text{DELETE\_PENALTY}\} \text{ for } p^* \text{ in } P[d]$$

$$i=M[j-1,d]+\text{INSERT\_PENALTY}$$

$$a=\max\{M[j-1,p^*]+\text{MATCH\_SCORE}\} \text{ for } p^* \text{ in } P[d], \text{ if } S[j]=d;$$

$$\max\{M[j-1,p^*]+\text{MISMATCH\_PENALTY}\} \text{ for } p^* \text{ in } P[d], \text{ if } S[j]\neq d \quad (6)$$

As described above, e is the highest of the alignments of the first j characters of S with the portions of the DAG up to, but not including, d, plus an additional DELETE_PENALTY. Accordingly, if d is not the first letter of the sequence of the node, then there is only one predecessor, p, and the alignment score of the first j characters of S with the DAG (up-to-and-including p) is equivalent to M[j,p]+ DELETE_PENALTY. In the instance where d is the first letter of the sequence of its node, there can be multiple possible predecessors, and because the DELETE_PENALTY is constant, maximizing [M[j, p*]+ DELETE_PENALTY] is the same as choosing the predecessor with the highest alignment score with the first j characters of S.

In equation (6), i is the alignment of the first j−1 characters of the string S with the DAG up-to-and-including d, plus an INSERT_PENALTY, which is similar to the definition of the insertion argument in SW (see equation 1).

Additionally, a is the highest of the alignments of the first j characters of S with the portions of the DAG up to, but not including d, plus either a MATCH_SCORE (if the jth character of S is the same as the character d) or a MISMATCH_PENALTY (if the jth character of S is not the same as the character d). As with e, this means that if d is not the first letter of the sequence of its node, then there is only one predecessor, i.e., p. That means a is the alignment score of the first j−1 characters of S with the DAG (up-to-and-including p), i.e., M[j−1,p], with either a MISMATCH_PENALTY or MATCH_SCORE added, depending upon whether d and the jth character of S match. In the instance where d is the first letter of the sequence of its node, there can be multiple possible predecessors. In this case, maximizing {M[j, p*]+ MISMATCH_PENALTY or MATCH_SCORE} is the same as choosing the predecessor with the highest alignment score with the first j−1 characters of S (i.e., the highest of the candidate M[j−1,p*] arguments) and adding either a MISMATCH_PENALTY or a MATCH_SCORE depending on whether d and the jth character of S match.

Again, as in the SW algorithm, the penalties, e.g., DELETE_PENALTY, INSERT_PENALTY, MATCH_SCORE and MISMATCH_PENALTY, can be adjusted to encourage alignment with fewer gaps, etc.

As described in the equations above, the algorithm finds the optimal (i.e., maximum) value for each read by calculating not only the insertion, deletion, and match scores for that element, but looking backward (against the direction of the DAG) to any prior nodes on the DAG to find a maximum score. Thus, the algorithm is able to traverse the different paths through the DAG, which contain the known mutations. Because the graphs are directed, the backtracks, which move against the direction of the graph, follow the preferred isoform toward the origin of the graph, and the optimal alignment score identifies the most likely alignment within a high degree of certainty.

Implementation of the disclosed algorithm is exemplified in FIG. 1, where a sequence "ATCGAA" is aligned against a DAG that represents a reference sequence TTGGATATGGG (SEQ ID NO: 1) and a known insertion event TTGGATCGAATTATGGG (SEQ ID NO: 2), where the insertion is underlined.

FIG. 1 shows a pictorial representation of the read ("ATCGAA") being compared to the DAG. The top area of FIG. 1 presents a reference sequence TTGGATATGGG (SEQ ID NO: 1) and a known insertion event TTGGATCGAATTATGGG (SEQ ID NO: 2) (here, the insertion is underlined). The bottom area of FIG. 1 shows the alignment constructed using a DAG. In the depicted DAG, SEQ ID NOS. 1 and 2 can both be read by reading from the 5' end of the DAG to the 3' end of the DAG, albeit along different paths. The sequence read is shown as aligning to the upper path as depicted.

Figure 2:
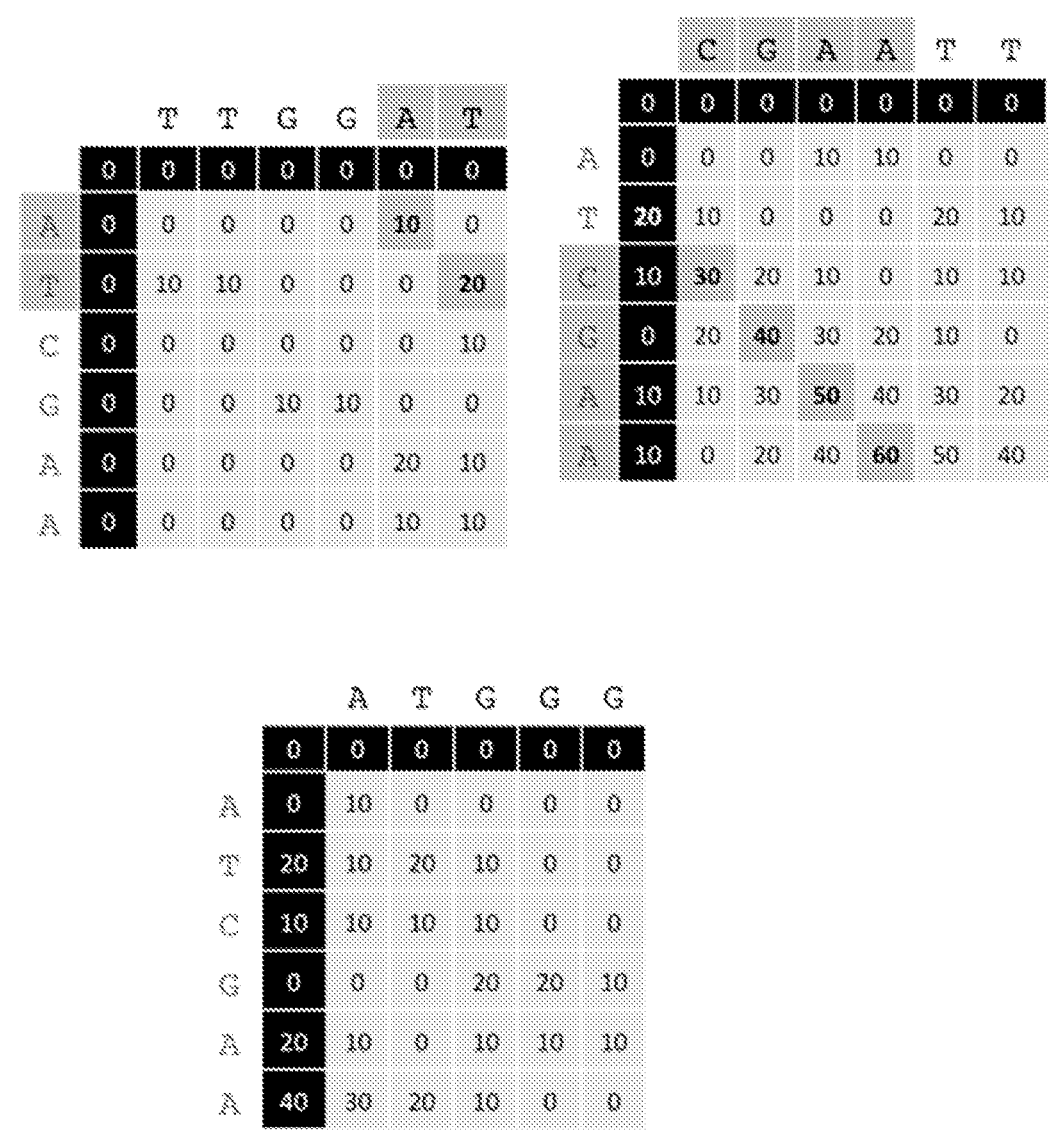

FIG. 2 shows the actual matrices that correspond to the comparison. Like the Smith-Waterman technique, the illustrated algorithm of the invention identifies the highest score and performs a backtrack to identify the proper location of the read. FIGS. 1 and 2 also highlight that the invention produces an actual match for the string against the construct. In the instances where the sequence reads include variants that were not included in the DAG, the aligned sequence will be reported out with a gap, insertion, etc.

One sequence DAG can be aligned to another sequence DAG to generate an aligned DAG by generalizing the foregoing in a method that includes first calculating values for entries in an array of pairwise match scores between characters from the respective sequence DAGs and then tracing along series of adjacent, associated elements in that array to find best-scoring alignments between paths through the respective DAGs. All of those resulting best-scoring alignments can be presented or stored as an aligned DAG. The aligned DAG is the aligned combination of the two sequence DAGs and is structurally similar to any of the original DAGs except that the input to the aligned DAG is always two or more DAGs as opposed to linear sequence. The aligned DAG can further be aligned to other DAGs or other aligned DAGs as described below The algorithmic modifications one must apply to the string-to-DAG algorithm in order to get a DAG-to-DAG algorithm are analogous to those applied to the string-to-string algorithm in order to get a string-to-DAG algorithm. In that case, we replaced terms such as i−1, where i represents an index, with P[i], where P[i] represents all immediate predecessors of the node with index i. One way to think about the modification is that finding the character with location i−1 in a string is a special case of picking out the set of predecessors: in a (linear) string, there is only one predecessor to the location with index i, and that is the location with index i−1, so insofar as a dynamic programming algorithm requires the consideration of some value for all predecessors of a location with index i, we can simply examine that value for the location with index i−1.

Considering the string-to-DAG equations as they appear above, we notice that various "j−1" terms, where j represents the index of a location in a string, still appear. Just as we moved from i−1 to P[i] in order to get the full set of predecessors in a DAG, we need to move from j−1 to P[j] to get the full set of predecessors of the object that is being aligned to the DAG, since this is no longer a string but itself a DAG. Thus, for example, we replace the e-term that is currently:

$e=\max\{M[j,p^*]+\text{DELETE\_PENALTY}\}$ for $p^*$ in $P[d]$ with:

$e=\max\{M[p^*,p^{**}]+\text{DELETE\_PENALTY}\}$ for $p^*$ in $P[d]$ and $p^{**}$ in $P[d']$ Other terms are to be modified analogously, so that we have:

$M[j,d]=\max\{a,i,e,O\}$ where $e=\max\{M[p^*,p^{**}]+\text{DELETE\_PENALTY}\}$ for $p^*$ in $P[j]$ and $p^{**}$ in $P[d]$ $i=\max\{M[p^*,d]+\text{INSERT\_PENALTY}\}$ for $p^*$ in $P[j]$ $a=\max\{M[p^*,p^{**}]+\text{MATCH\_SCORE}\}$ for $p^*$ in $P[j]$ & $p^{**}$ in $P[d]$, if $S[j]=d;\max\{M[p^*,p^{**}]+\text{MISMATCH\_PENALTY}\}$ for $p^*$ in $P[j]$ and $p^{**}$ in $P[d]$, if $S[j]\ne d$ Although it is common to consider alignments of one string to another, and although we have shown how to generalize this process by replacing strings with DAGs, most people think of a process or result, not an object, when they speak of "alignments." We observe, however, that the output of an alignment process, because it contains information about the relationship of one genetic item to another, can be represented not only as a located string or a compact idiosyncratic gapped alignment report (CIGAR) string, e.g., a CIGAR string in a BAM format file, but also as a DAG. For discussion of file formats, see Li, et al., 2009, The Sequence Alignment/Map format and SAMtools, Bioinformatics 25(16):2078-9 and Li et al., 2009, SOAP2: an improved ultrafast tool for short read alignment, Bioinformatics 25(15):1966-7, both incorporated by reference.

Because DAG-to-DAG alignment is possible, and because alignments can be viewed as DAGs, it is possible to align alignments to alignments. A set of BAM entries, for example, can be converted to DAGs and aligned to each other. Indeed, BAMs that have been generated relative to different references can be aligned against each other. Given the quantity of existing BAM files and the variety of references to which those files correspond, the ability to directly compare entries from BAMs with different references would be valuable, and these techniques remove barriers to our gaining that ability.

One can convert a BAM entry to a DAG by using the relevant reference and the CIGAR string for the given entry, because BAM sequence entries, CIGAR strings, and references—taken together—contain enough information to construct a DAG representing the alignment. With reference to Table 1 of Li, et al., 2009, The Sequence Alignment/Map format and SAMtools, Bioinformatics 25(16):2078-9, we see that the fourth mandatory field in the SAM format is POS, 1-Based leftmost POSition of clipped alignment.

Suppose that in a given BAM entry, we have in the SEQ field:

GATTACACATGATTACATGACTGACCATTCCAT  (SEQ ID NO: 3)

The POS field tells us to look at position 1,525,334 in the reference, where we find:

(SEQ ID NO: 4)
GAGTACAGATTACATGACTGACGGAGCATTACATCT . . .

In the CIGAR field, we find:
M7I3M15D4M8

We begin by examining the first seven characters of each sequence, because those correspond to portions that aligned to each other. Note that this does not entail that there are no mismatches:

GATTACA

GAGTACA

We see that there is a mismatch in position 3.

Figure 3:
FIG. 3 illustrates a DAG that obtains from a first step in building a sequence DAG.
Figure 3:
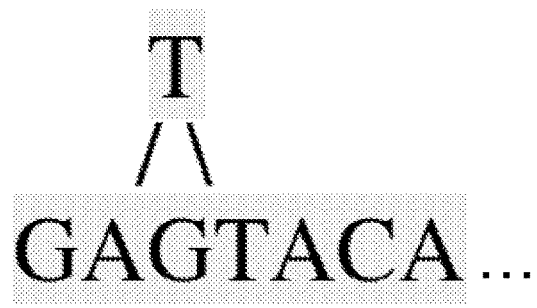
Figure 4:
FIG. 4 shows how an initial DAG is built up by alignment.
Figure 5:
FIG. 5 shows a DAG continuing to grow.
Figure 5:
Figure 6:
FIG. 6 illustrates a sequence DAG that is nearly complete.
Figure 6:
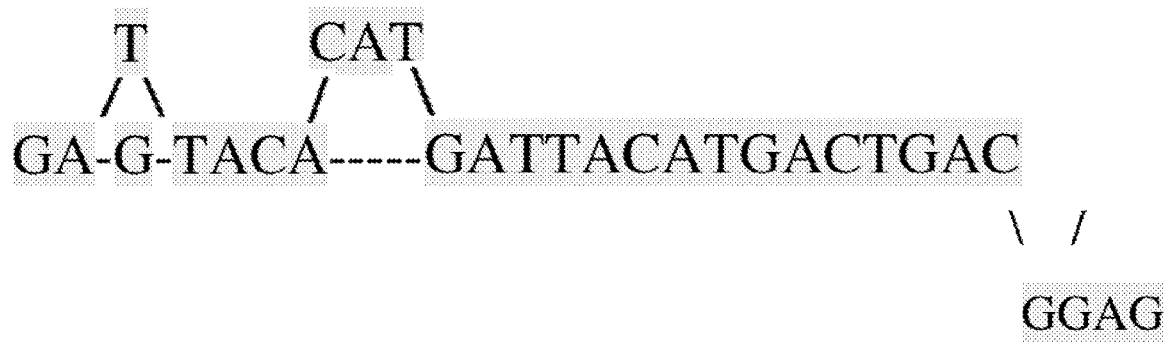
Figure 7:
FIG. 7 depicts the complete DAG.
Figure 7:
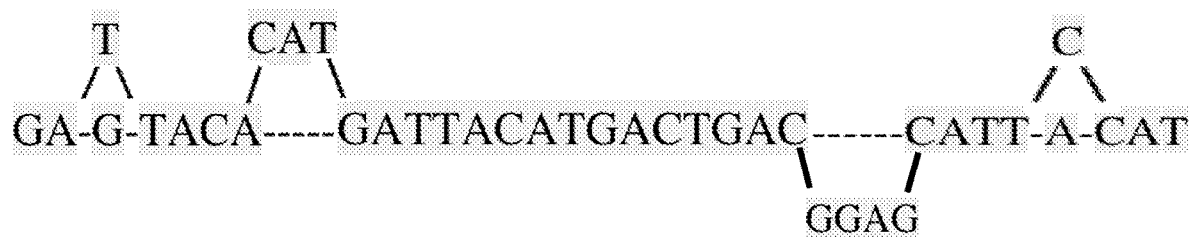

FIG. 3 illustrates the DAG that is produced from a first step in building a sequence DAG. The "13" portion of the CIGAR string indicates an insertion of three bases, so we can continue. FIG. 4 shows the DAG that represents a DAG as it grows. The "M15" indicates that the next fifteen characters of each string are aligned as a group. These indeed match, so we continue. FIG. 5 illustrates the DAG resulting from this step. The "D4" indicates that the next four bases from the reference are deleted, leading to the DAG shown in FIG. 6. FIG. 6 illustrates a sequence DAG as it is being built. Finally, the last eight bases are treated as an aligned unit, and we find one mismatch. This produces our final DAG, shown in FIG. 7. FIG. 7 depicts the complete DAG representing the alignment described by the hypothetical BAM entry.

That completed DAG as depicted in FIG. 7 is an example of a sequence DAG. The sequence DAG is created in a way that reflects the scoring given by a Smith-Waterman-type alignment algorithm and the sequence DAG can further be aligned to another sequence DAG.

Figure 8:
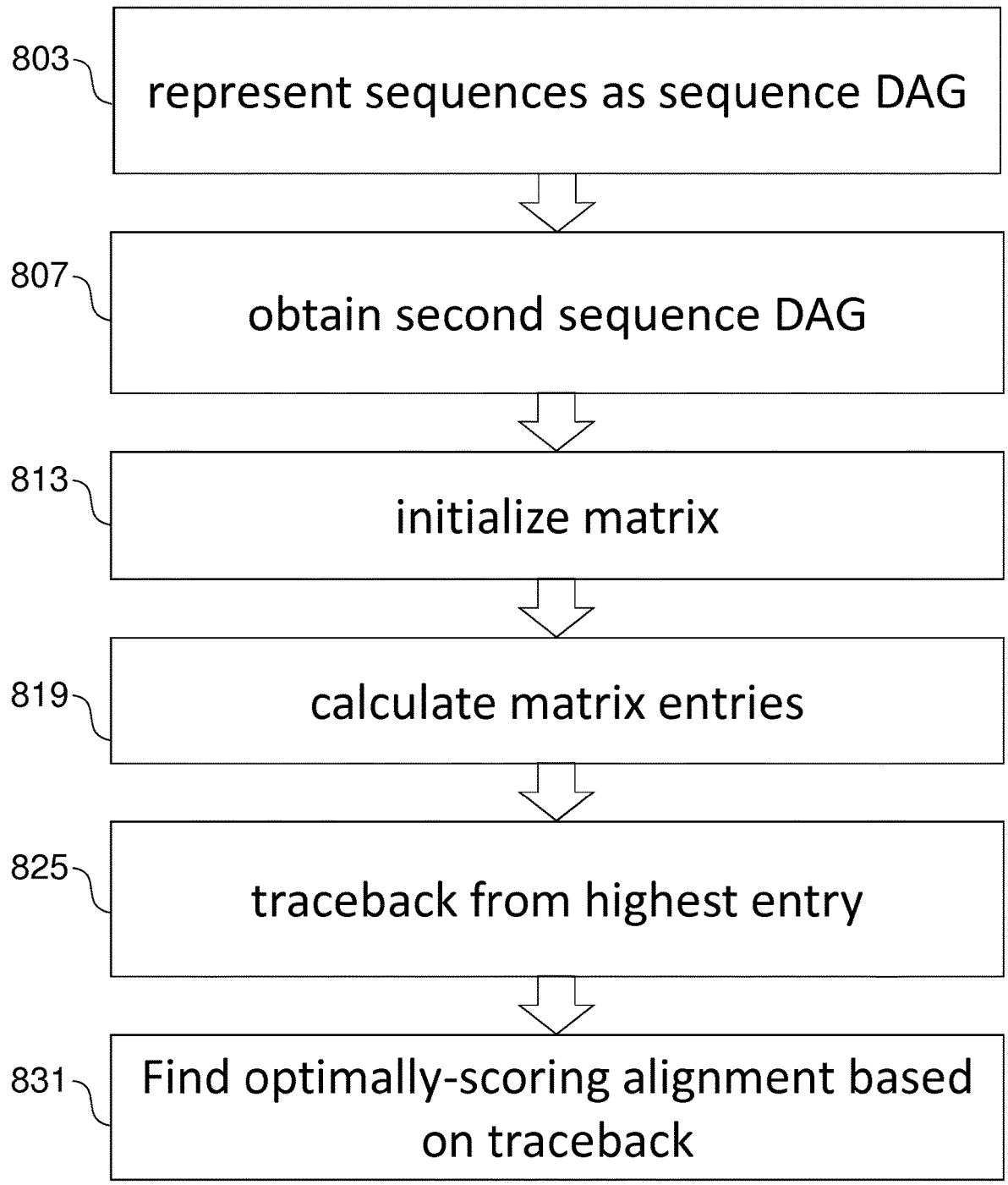
FIG. 8 diagrams a method of DAG-to-DAG alignment.

FIG. 8 diagrams a method of DAG-to-DAG alignment according to embodiments of the invention. In general, the method includes the following steps.

Represent 803 a plurality of nucleic acids as a reference directed acyclic graph (DAG), wherein a DAG comprises nodes, each node comprising a string of one or more nucleotides, and edges defining connections among the nodes, and further wherein one or more of the nodes each represent more than one of the plurality of nucleic acids.

Obtain 807 a second DAG representing a second plurality of nucleic acids.

Initialize 813 a matrix of similarities between nucleotides in the reference DAG and nucleotides in the second DAG by setting all edge entries to be zero, wherein an edge entry is an entry with no more than 1 non-zero index.

For each non-edge entry, associate that entry with a highest-value upstream neighbor entry of that entry and calculate 819 a value for that entry with a value based on the highest-value upstream neighbor entry, wherein an upstream neighbor entry has indices that each differ by −1 or 0, at least one index differing by −1, from the corresponding indices of that entry being populated.

Identify 831 a traceback path through the matrix that originates at the entry with the highest value and traces sequentially through each associated highest-value upstream neighbor until a zero entry is met at which zero entry the path terminates, wherein the identified path indicates the optimally-scoring alignment between the second DAG and the reference DAG.

Find an optimally-scoring alignment between the second DAG and the reference DAG. The alignment of one sequence DAG to another, as described, proceeds through the use of a matrix of similarities (or distances) and produces an aligned DAG. In that sense, the aligned DAG may be referred to as a "DAG matrix alignment" and so may the procedure of aligning sequences, sequence DAGs, or a combination thereof through the use of a similarity matrix to produce a DAG of aligned sequences may be referred to as performing a DAG matrix alignment.

One feature of the invention that is helpful to recognize is that methods of the invention may be used to find an alignment between two or more sequence DAGs and, depending on the nature or objectives of the work being done, the obtained alignment may be, but need not be, the "highest scoring" alignment nor even an optimally-scoring alignment. For example, some researchers may calculate both a similarity and a distance score by supplying different match and mismatch penalties. Since distance is a measure of a number of differences, and similarity is a measure of (roughly) a number of matches, the sign of the score would change depending on which is calculated. Further, where the two sequences TGC and TCC have certain a similarity score and a certain distance score, the two sequences TAACTAGC and TAACTACC would have the same distance score but a much higher similarity score.

3. Local Heuristic Assembly

A related but distinct innovation is "local heuristic assembly." This process could be used to solve a persistent problem in the analysis of short reads: that of inferring the sequences of repetitive regions, tandem duplications, indels, and other structural variants.

There are two major obstacles to such inference. First, structural variants are so large that reads are simply thrown away as unalignable rather than recognized as arising from a certain region. Second, repetitive regions will align so well to many locations that it can be difficult to know which of those many locations corresponds to the real origin of the read. These obstacles are somewhat independent; each can occur without the other. Many structural variants are, however, repetitive regions, and many repetitive regions are likely candidates for being inserted or deleted in one sample relative to another (which is why they are repetitive in the first place).

The invention provides systems and methods for inferring the sequences of repetitive regions, tandem duplications, indels, and other structural variants based on paired-end data. Methods of the invention include aligning a plurality of paired-end reads to the reference, identifying a set of unaligned reads from the plurality of paired-end reads that did not align to the reference according to some criterion, and—for the set of unaligned reads—finding clusters of those unaligned paired-end reads for which a portion of reads map to the same part of the genome.

Any suitable method may be used find the clusters. Once one has mapped the beginnings of (paired-end) reads as far as they can be mapped, and associated those beginnings-of-reads with genomic locations, any known clustering method could in theory be used to sort those into clusters. In practice, it will likely be more reasonable simply to search for windows of R base pairs in which sufficiently many reads map. (We might take R to be equal to read length of a given set of short reads.). Clusters, in cases both of split reads and read-pairs, are discussed and illustrated in Stewart, et al., 2011, A comprehensive map of mobile element insertion polymorphisms in humans, PLoS Genetics 7(8):1-19, incorporated by reference.

Figure 9:
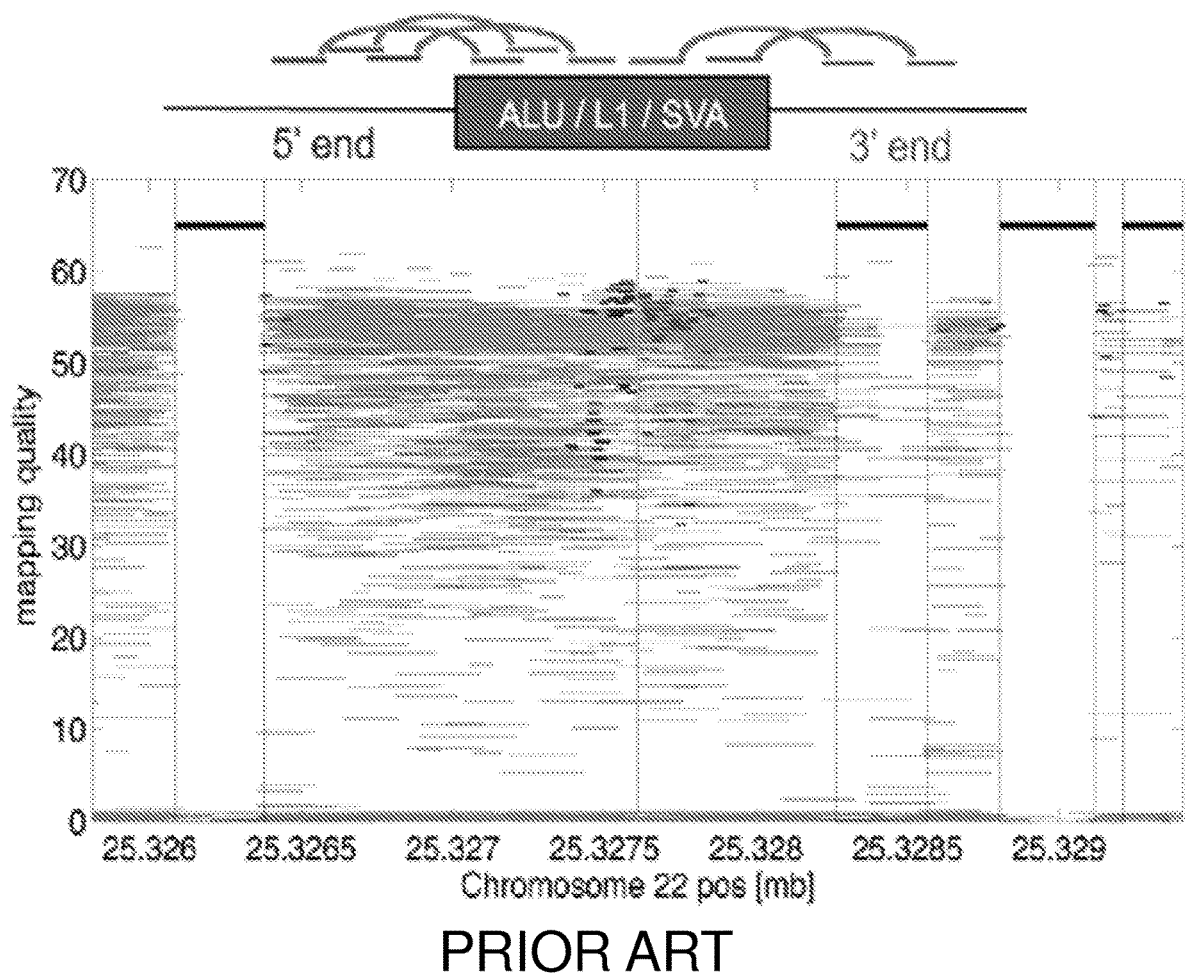
FIG. 9 shows a prior art approach to detecting structural variants.

FIG. 9, reproduced from FIG. 1 in Stewart, et al., 2011, A comprehensive map of mobile element insertion polymorphisms in humans, PLoS Genetics 7(8):1-19, illustrates a prior art method for the detection of non-reference mobile element inserts (MEI). That method can use a read-pair constraint (RP) method applied to Illumina paired-end short read data and a split-read (SR) method applied to the longer read data from Roche/454 pyrosequencing. FIG. 9 shows the detection signatures and examples of event displays by RP detection. Candidate MEI events were formed as clusters of supporting fragments. A limitation specific to RP detection arises from annotated elements within a characteristic read pair fragment length of candidate MEI. Read pairs spanning from a uniquely mapped anchor into an annotated mobile element with a fragment length consistent with the given library fragment length distribution are characteristic of the reference allele and are not evidence for non-reference MEI.

FIG. 9 shows a prior art RP signature for of non-reference MEI detection. The RP signature consists of Illumina read pairs spanning into the element from each side of the insertion. The RP event display shows a heterozygous Alu insertion allele on chromosome 22 from a pilot dataset. Fragment mapping quality is shown on the vertical scale. Horizontal lines show read pairs uniquely mapped at both ends with a mapped fragment length consistent with the sequence library; the short lines at the outer ends of the arc-shaped lines are read pairs spanning into an Alu sequence from the 5' and 3' ends. The central vertical line is the position of the insertion. Thick lines near the top show annotated Alu positions. Thus, FIG. 8 illustrates a clusters of paired-end reads for which a portion of reads map to the same part of the genome for the RP case. Clusters may also be found in the SR case or in other contexts.

For each cluster, methods include filtering the reads so that the mapped and unmapped portions are at least a base pairs long, where a is a constant chosen beforehand (it might be reasonable to choose a=10) and sorting the unmapped portions according to their expected left- to-right (where 'leftness' corresponds to smaller indices and 'rightness' greater indices according to some indexing scheme) positions. This can be deduced from the read length, the insert size, and the length of the mapped portions.

As used herein, insert size is generally taken to refer to length of a nucleic acid molecule being sequenced. Thus an insert size may be, for example, 500 base pairs, with a read length of 100 base pairs. Then the distance between the reads is approximately 300 base pairs, so that if the mapped portion is greater than 100 base pairs, the expected starting position of the yet-to-be-mapped portion is (the starting position of the mapped portion+100+300+(the length of the mapped portion−100)), which equals (the starting position of the mapped portion+300+ the length of the mapped portion). If the mapped portion is shorter than the sequence length, there figure to be two unmapped portions, one of which begins at (the starting position of the mapped portion+ the length of the mapped portion) and the other of which begins at (the starting position of the mapped portion+100+300), which equals (the starting position of the mapped portion+400). It is recognized that in some instances in the literature, "insert size" is used to refer to the space between reads. However, method described herein are equally applicable regardless of how "insert size" is used by making the appropriate adjustments in language usage.

Methods further include, for each cluster taking the first ("first" according to the sorting procedure, that is) unmapped portion and consider it as a reference object. Although it is a string, take it to be a (flat) DAG. Call it R.

For each remaining unmapped read-portion, in sorted order: align that read-portion to R; create a DAG representing that alignment; and update R to be the DAG created in the preceding step.

The result is a raw local assembly—a DAG representing the region about which the original alignment process did not give information. Therefore, this process makes important improvements over the status quo. It will give accurate sequence information about indels and structural variants that existing tools do not resolve or altogether ignore. One can further refine this assembly DAG into haplotypes.

4. Applications to Haplotyping

By haplotype we mean here set of nearby variants inherited (usually) together and able to be considered as a unit. A process of determining haplotypes in a sample can be used along with the process described above, and any related process whereby many reads (or alignments) are sequentially aligned to a reference object, which thereby accumulates information.

Note first that haplotypes can be represented as paths through a DAG. A process of determining relevant haplotypes is therefore expressible as a process of determining relevant paths through a DAG.

The invention provides systems and methods for determining relevant haplotypes from a sequence DAG. Methods include aligning reads to a DAG and tracking how many reads are consistent with each location within the DAG and defining the support of a node in the DAG as the number of reads consistent with it. By extension, the support of a path through the DAG is defined as the minimum of the support values of each of the nodes in that path.

Once support for each of a plurality of paths through the DAG has been determined according to a number of reads consistent with a location in that path that is consistent with fewer reads than any other location in that path, then a number of the paths meeting a pre-determined support criteria may be identified as describing relevant haplotypes.

In certain embodiments, the foregoing steps may include the following specific methodological steps. Let n be the number of paths with support greater than or equal to some constant chosen before the process (perhaps 3% of the number of reads divided by the number of samples from which the reads were drawn). Let k be two times the number of human genomes represented in the set from which the reads were drawn. If n is less than or equal to k, then each of the n paths is a "relevant" haplotype. (Throughout this discussion, "relevant" means "evidentially supported in the sample to such a degree that one can posit its existence in the source of the sample.") Otherwise, the k best-supported haplotypes are the relevant ones.

5. Systems of the Invention.

Figure 10:
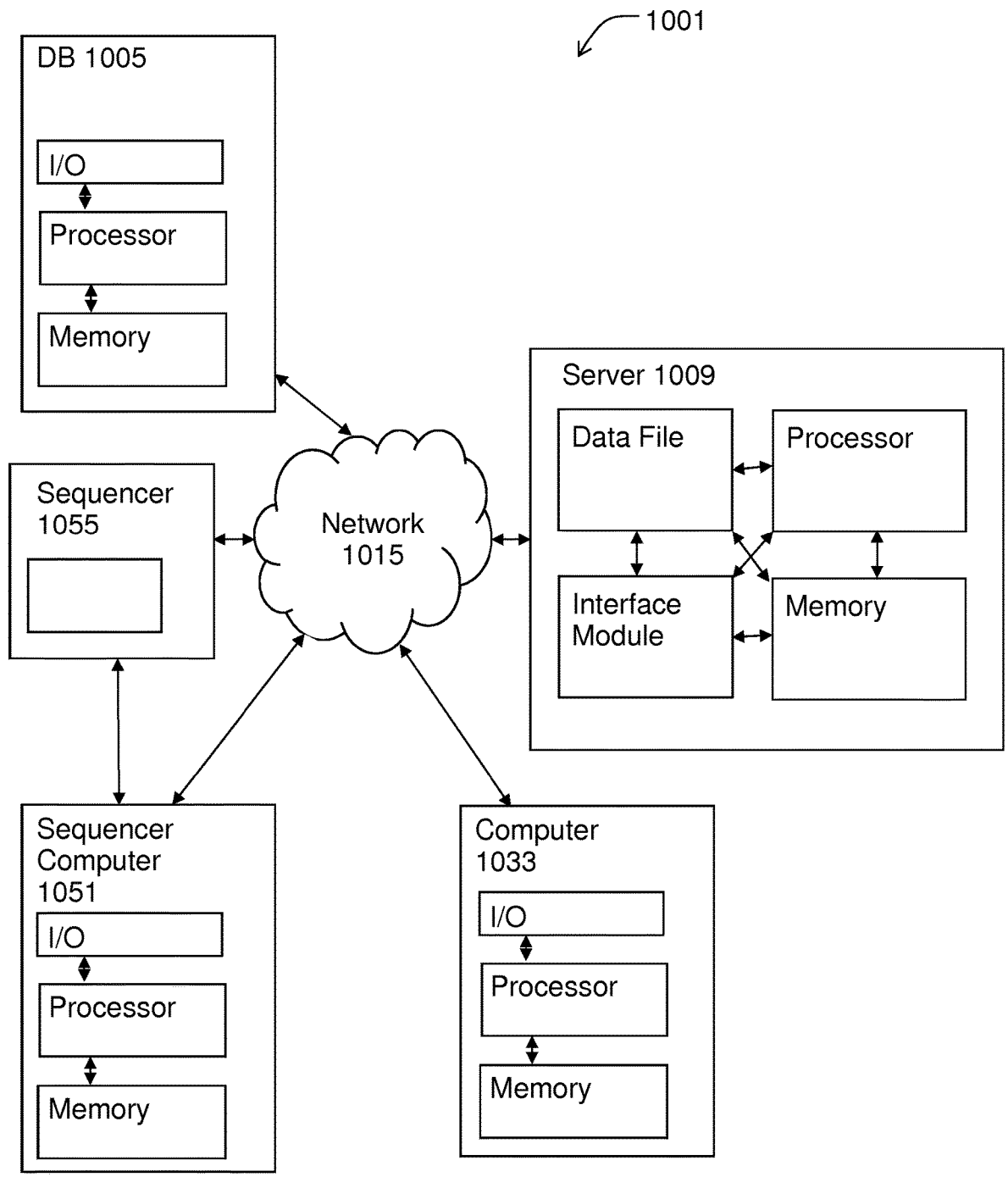
FIG. 10 illustrates a computer system according to embodiments of the invention.

FIG. 10 illustrates a computer system 1001 useful for implementing methodologies described herein. A system of the invention may include any one or any number of the components shown in FIG. 10. Generally, a system 1001 may include a computer 1033 and a server computer 1009 capable of communication with one another over network 1015.

Additionally, data may optionally be obtained from a database 1005 (e.g., local or remote). In some embodiments, systems include an instrument 1055 for obtaining sequencing data, which may be coupled to a sequencer computer 1051 for initial processing of sequence reads.

In some embodiments, methods are performed by parallel processing and server 1009 includes a plurality of processors with a parallel architecture, i.e., a distributed network of processors and storage capable of comparing a first sequence DAG to a second sequence DAG. The system comprises a plurality of processors that simultaneously execute a plurality of comparisons between a plurality of reads and the reference sequence construct. While other hybrid configurations are possible, the main memory in a parallel computer is typically either shared between all processing elements in a single address space, or distributed, i.e., each processing element has its own local address space. (Distributed memory refers to the fact that the memory is logically distributed, but often implies that it is physically distributed as well.) Distributed shared memory and memory virtualization combine the two approaches, where the processing element has its own local memory and access to the memory on non-local processors. Accesses to local memory are typically faster than accesses to non-local memory.

Processor-processor and processor-memory communication can be implemented in hardware in several ways, including via shared (either multiported or multiplexed) memory, a crossbar switch, a shared bus or an interconnect network of a myriad of topologies including star, ring, tree, hypercube, fat hypercube (a hypercube with more than one processor at a node), or n-dimensional mesh.

Parallel computers based on interconnected networks incorporate routing to enable the passing of messages between nodes that are not directly connected. The medium used for communication between the processors is likely to be hierarchical in large multiprocessor machines. Such resources are commercially available for purchase for dedicated use, or these resources can be accessed via "the cloud," e.g., Amazon Cloud Computing.

One approach to parallelizing Smith-Waterman-type alignments is discussed in Altera, 2007, Implementation of the Smith-Waterman algorithm on reconfigurable supercomputing platform, White Paper ver 1.0 (18 pages), incorporated by reference.

A computer generally includes a processor coupled to a memory and an input-output (I/O) mechanism via a bus. Memory can include RAM or ROM and preferably includes at least one tangible, non-transitory medium storing instructions executable to cause the system to perform functions described herein. As one skilled in the art would recognize as necessary or best-suited for performance of the methods of the invention, systems of the invention include one or more processors (e.g., a central processing unit (CPU), a graphics processing unit (GPU), etc.), computer-readable storage devices (e.g., main memory, static memory, etc.), or combinations thereof which communicate with each other via a bus.

A processor may be any suitable processor known in the art, such as the processor sold under the trademark XEON E7 by Intel (Santa Clara, Calif.) or the processor sold under the trademark OPTERON 6200 by AMD (Sunnyvale, Calif.).

Input/output devices according to the invention may include a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for inferring a sequence part of a non-reference genome of a first organism based on paired-end sequence read data, the method comprising using at least one computer hardware processor to perform:
- aligning a plurality of paired-end reads from the non-reference genome of the first organism to a reference genome of a second organism to obtain an alignment, the non-reference genome of the first organism including a first region comprising at least one structural variant relative to the reference genome of the second organism;
- identifying, from among the plurality of paired-end reads and using the alignment, a first set of paired-end reads comprising paired-end reads each having an aligned read and an unaligned read;
- identifying a second set of paired-end reads from among the first set of paired-end reads, wherein aligned reads of the second set map to an overlapping anchor region of the reference genome, and wherein unaligned reads of the second set overlap with the first region of the non-reference genome; and
- aligning at least some of the unaligned reads of the second set against one another to create a directed acyclic graph (DAG) representing a local assembly for the first region of the non-reference genome, wherein the aligning comprises:
  - creating an initial DAG representing a first unaligned read of the at least some of the unaligned reads;
  - aligning the at least some of the unaligned reads other than the first unaligned read to the initial DAG to obtain an alignment among the at least some of the unaligned reads; and
  - updating the initial DAG to represent the alignment among the at least some of the unaligned reads, thereby creating the DAG representing the local assembly for the first region of the non-reference genome.

2. The method of claim 1, wherein identifying the second set of paired-end reads further comprises searching for windows of the alignment in which a sufficient number of aligned reads map.

3. The method of claim 2, wherein the window size is about the read length.

4. The method of claim 1, wherein identifying the second set of paired-end reads further comprises identifying a region of the genome showing a read-pair constraint (RP) signature.

5. The method of claim 1, further comprising sorting the at least some of the unaligned reads of the second set according to their expected left-to-right positions.

6. The method of claim 5, wherein the expected left-to-right position for an unaligned read of a first read pair of the second set is deduced from a position of an aligned read of the first read pair and an insert size.

7. The method of claim 1, wherein aligning the at least some of the unaligned reads to the initial DAG comprises:
- identifying a difference at a position in the initial DAG between the first unaligned read and a second unaligned read of the at least some of the unaligned reads, and
- building an updated DAG in which the difference is represented as an alternate path from the first unaligned read.

8. The method of claim 7, wherein the difference is identified from a CIGAR string representing the alignment among the at least some of the unaligned reads.

9. The method of claim 1, further comprising refining the DAG representing the local assembly of the first region of the non-reference genome into a haplotype sequence representing the first region of the non-reference genome.

10. The method of claim 9, wherein refining the DAG representing the local assembly for the first region of the non-reference genome comprises identifying a path through the DAG.

11. The method of claim 9, wherein the haplotype sequence comprises a repetitive region, a tandem duplication, an indel, or other structural variation.

12. A system for inferring a sequence part of a non-reference genome of a first organism based on paired-end sequence read data, the system comprising:
- at least one computer hardware processor; and
- at least one non-transitory computer-readable storage medium storing processor-executable instructions that, when executed by the at least one computer hardware processor, cause the at least one computer hardware processor to perform:
  - aligning a plurality of paired-end reads from the non-reference genome of the first organism to a reference genome of a second organism to obtain an alignment, the non-reference genome of the first organism including a first region comprising at least one structural variant relative to the reference genome of the second organism;
  - identifying, from among the plurality of paired-end reads and using the alignment, a first set of paired-end reads comprising paired-end reads each having an aligned read and an unaligned read;
  - identifying a second set of paired-end reads from among the first set of paired-end reads, wherein the aligned reads of the second set map to an overlapping anchor region of the reference genome, and wherein the unaligned reads of the second set overlap with the first region of the non-reference genome; and
  - aligning at least some of the unaligned reads of the second set against one another to create a directed acyclic graph (DAG) representing a local assembly for the first region of the non-reference genome, wherein the aligning comprises:
    - creating an initial DAG representing a first unaligned read of the at least some of the unaligned reads;
    - aligning the at least some of the unaligned reads other than the first unaligned read to the initial DAG to obtain an alignment among the at least some of the unaligned reads; and
    - updating the initial DAG to represent the alignment among the at least some of the unaligned reads, thereby creating the DAG representing the local assembly for the first region of the non-reference genome.

13. The system of claim 12, wherein identifying the second set of paired-end reads further comprises searching for windows of the alignment in which a sufficient number of aligned reads map.

14. The system of claim 12, wherein identifying the second set of paired-end reads further comprises identifying a region of the genome showing a read-pair constraint (RP) signature.

15. The system of claim 12, further comprising sorting the at least some of the unaligned reads of the second set according to their expected left-to-right positions.

16. The system of claim 15, wherein the expected left-to-right position for an unaligned read of a first read pair of the second set is deduced from a position of an aligned read of the first read pair and an insert size.

17. The system of claim 12, wherein aligning the at least some of the unaligned reads to the initial DAG comprises:
identifying a difference at a position in the initial DAG between the first unaligned read and a second unaligned read of the at least some of the unaligned reads, and
building an updated DAG in which the difference is represented as an alternate path from the first unaligned read.

18. The system of claim 12, further comprising refining the DAG representing the local assembly for the first region of the non-reference genome into a haplotype sequence representing the first region of the non-reference genome.

19. The system of claim 18, wherein refining the DAG representing the local assembly for the first region of the non-reference genome comprises identifying a path through the DAG.

20. At least one non-transitory computer-readable storage medium storing processor executable instructions that, when executed by at least one computer hardware processor, cause the at least one computer hardware processor to perform a method for inferring a sequence part of a non-reference genome of a first organism, the method comprising:
aligning a plurality of paired-end reads from the non-reference genome of the first organism to a reference genome of a second organism to obtain an alignment, the non-reference genome of the first organism including a first region comprising at least one structural variant relative to the reference genome of the second organism;
identifying, from among the plurality of paired-end reads and using the alignment, a first set of paired-end reads comprising paired-end reads each having an aligned read and an unaligned read;
identifying a second set of paired-end reads from among the first set of paired-end reads, wherein the aligned reads of the second set map to an overlapping anchor region of the reference genome, and the unaligned reads of the second set overlap with the first region of the non-reference genome; and
aligning at least some of the unaligned reads of the second set against one another to create a directed acyclic graph (DAG) representing a local assembly for the first region of the non-reference genome, wherein the aligning comprises:
creating an initial DAG representing a first unaligned read of the unaligned reads;
aligning the at least some of the unaligned reads other than the first unaligned read to the initial DAG to obtain an alignment among the at least some of the unaligned reads; and
updating the initial DAG to represent the alignment among the at least some of the unaligned reads, thereby creating the DAG representing the local assembly for the first region of the non-reference genome.

* * * * *